US010959643B2

(12) United States Patent
Osadchy et al.

(10) Patent No.: US 10,959,643 B2
(45) Date of Patent: Mar. 30, 2021

(54) SENSOR FOR FACILITATING CATHETER VISUALIZATION

(71) Applicant: BIOSENSE WEBSTER (ISRAEL) LTD., Yokneam (IL)

(72) Inventors: Daniel Osadchy, Haifa (IL); Konstantin Feldman, Haifa (IL); Assaf Pressman, Pardes Hanna-Karkur (IL); Shmuel Cohen, Yokneam Illit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 921 days.

(21) Appl. No.: 15/469,895

(22) Filed: Mar. 27, 2017

(65) Prior Publication Data
US 2018/0271402 A1 Sep. 27, 2018

(51) Int. Cl.
*A61B 5/06* (2006.01)
*A61B 5/00* (2006.01)
*A61B 5/0536* (2021.01)
*A61B 5/042* (2006.01)
*A61B 17/00* (2006.01)
*A61B 34/20* (2016.01)

(52) U.S. Cl.
CPC ............ *A61B 5/068* (2013.01); *A61B 5/0044* (2013.01); *A61B 5/0422* (2013.01); *A61B 5/0536* (2013.01); *A61B 5/063* (2013.01); *A61B 5/06* (2013.01); *A61B 5/061* (2013.01); *A61B 2017/00243* (2013.01); *A61B 2034/2051* (2016.02); *A61B 2034/2053* (2016.02)

(58) Field of Classification Search
CPC ..... A61B 5/068; A61B 5/0422; A61B 5/0044; A61B 5/0536; A61B 5/063; A61B 5/06; A61B 5/061; A61B 2034/2051; A61B 2034/2053; A61B 2017/00243; A61M 25/0662; A61M 2025/0681
See application file for complete search history.

(56) References Cited

U.S. PATENT DOCUMENTS

| 5,383,874 | A | 1/1995 | Jackson et al. |
| 8,343,096 | B2 | 1/2013 | Kirschenman et al. |
| 8,456,182 | B2 | 6/2013 | Bar-Tal et al. |
| 2003/0047556 | A1* | 3/2003 | Horey ................. H05B 1/0272 219/497 |
| 2006/0004286 | A1* | 1/2006 | Chang .................... A61B 34/20 600/435 |
| 2006/0189867 | A1* | 8/2006 | Revie .................... A61B 90/10 600/424 |

(Continued)

FOREIGN PATENT DOCUMENTS

| EP | 2 740 432 A2 | 6/2011 |
| EP | 3 106 195 A2 | 12/2016 |

OTHER PUBLICATIONS

European Search Report dated Jun. 13, 2018, Application No. 18163895.8.

*Primary Examiner* — Peter Luong

(57) ABSTRACT

Described embodiments include apparatus for use with a catheter. The apparatus includes a sheath configured for insertion into a body of a subject, and a sensor, coupled to the sheath, configured to detect an electric current passing through the catheter, when the catheter passes through the sheath and into the body of the subject. Other embodiments are also described.

16 Claims, 2 Drawing Sheets

(56) References Cited

U.S. PATENT DOCUMENTS

| | | | |
|---|---|---|---|
| 2008/0278575 A1* | 11/2008 | Matsui | A61B 1/00009 |
| | | | 348/72 |
| 2009/0248042 A1 | 10/2009 | Kirschenman | |
| 2009/0264739 A1 | 10/2009 | Markowitz et al. | |
| 2012/0035674 A1 | 2/2012 | Weinstock | |
| 2014/0275991 A1 | 9/2014 | Potter et al. | |
| 2015/0126895 A1 | 5/2015 | Lichtenstein | |

* cited by examiner

SENSOR FOR FACILITATING CATHETER VISUALIZATION

FIELD OF THE INVENTION

The present invention relates to the field of medical apparatus and procedures, and particularly to apparatus for facilitating the visualization of a catheter during a procedure.

BACKGROUND

In various types of medical procedures, such as cardiac mapping and ablation procedures, a sheath is inserted into the subject's body, and a catheter is then passed through the sheath. The sheath may facilitate navigation of the catheter to the desired location within the subject's body.

US Patent Application Publication 2009/0248042, whose disclosure is incorporated herein by reference, describes an input device for a robotic medical system, including a sheath handle, comprising a flexible shaft defining a lumen therein. The input device also includes a catheter handle comprising a second flexible shaft which is at least partially disposed within the lumen of the first shaft. The sheath handle and the catheter handle are each coupled to a plurality of respective guide wires, which are configured such that movement of the handles causes a corresponding tension response in one or more of the plurality of guide wires. Sensors are connected to the guide wires to measure the movement of the sheath handle and the catheter handle.

U.S. Pat. No. 8,343,096, whose disclosure is incorporated herein by reference, describes a robotic catheter system including one or more robotic catheter manipulator assemblies supported on a manipulator support structure. The robotic catheter manipulator assembly may include one or more removably mounted robotic catheter device cartridges and robotic sheath device cartridges, with each cartridge being generally linearly movable relative to the robotic catheter manipulator assembly. An input control system may be provided for controlling operation of the robotic catheter manipulator assembly. A visualization system may include one or more display monitors for displaying a position of a catheter and/or a sheath respectively attached to the robotic catheter and sheath device cartridges.

SUMMARY OF THE INVENTION

There is provided, in accordance with some embodiments of the present invention, apparatus for use with a catheter. The apparatus includes a sheath configured for insertion into a body of a subject, and a sensor, coupled to the sheath, configured to detect an electric current passing through the catheter, when the catheter passes through the sheath and into the body of the subject.

In some embodiments, the sheath includes a proximal portion, and the sensor is coupled to the proximal portion of the sheath.

In some embodiments, the sensor is disposed within the proximal portion of the sheath.

In some embodiments, the proximal portion of the sheath includes a handle, and the sensor is disposed within the handle.

In some embodiments, the sensor includes a coil.

In some embodiments, the sensor further includes a ferrite toroid, the coil being wound around the ferrite toroid.

In some embodiments, the apparatus further includes a processor, configured to ascertain, responsively to the sensor detecting the electric current, that the catheter passes through the sheath.

In some embodiments, the processor is further configured to display a representation of a distal portion of the catheter emerging from the sheath, responsively to ascertaining that the catheter passes through the sheath.

In some embodiments, the processor is configured:
to identify a location, relative to the body of the subject, of the distal portion of the catheter,
to display an image of an interior of the body of the subject, and
to display the representation of the distal portion of the catheter emerging from the sheath by superimposing the representation on a portion of the image corresponding to the identified location.

In some embodiments, the processor is configured to identify the location of the distal portion of the catheter responsively to the electric current being passed from an electrode at the distal portion of the catheter.

In some embodiments, the sheath includes a distal portion, and the processor is configured:
to identify a location, relative to the body of the subject, of the distal portion of the sheath,
to display an image of an interior of the body of the subject, and
to display the representation of the distal portion of the catheter emerging from the sheath by superimposing the representation on a portion of the image corresponding to the identified location.

In some embodiments, the apparatus further includes one or more electrodes coupled to the distal portion of the sheath, and the processor is configured to identify the location of the distal portion of the sheath responsively to electric currents passed from the electrodes.

In some embodiments, the processor is further configured to identify the catheter from a plurality of catheters, responsively to a frequency of the electric current detected by the sensor.

There is further provided, in accordance with some embodiments of the present invention, a method that includes, using a sensor that is coupled to a sheath, detecting an electric current passing through a catheter, when the catheter passes through the sheath and into a body of a subject. The method further includes, using a processor, ascertaining, responsively to the sensor detecting the electric current, that the catheter passes through the sheath.

The present invention will be more fully understood from the following detailed description of embodiments thereof, taken together with the drawings, in which:

DETAILED DESCRIPTION OF EMBODIMENTS

Overview

In embodiments of the present invention, an active current location (ACL) system is used to track a medical device, such as a catheter or sheath, inside the body of a subject. In the ACL system, electric currents are passed between internal electrodes coupled to the distal portion of the device and external electrodes located outside of the subject's body, such as electrode patches coupled to the subject's chest and/or back. The internal electrodes pass currents at different respective frequencies, such that the impedance between each pair of electrodes may be separately ascertained. Based on these impedances, the respective locations of the internal electrodes may be ascertained. A representation of the distal portion of the device may then be displayed on a display, at the location, and with the orientation, implied by the ascertained electrode locations.

In some cases, the ACL system may be used to track both a catheter and a sheath, while both are inside the body at the same time. A challenge, in such a case, is that it may be unclear if the catheter is passing through the sheath, or is, instead, passing alongside the sheath.

To address this challenge, embodiments of the present invention provide a current or voltage sensor disposed within the handle of the sheath. When a catheter passes through the sheath, and ACL currents are passed from the proximal end of the catheter to the electrodes at the distal portion of the catheter, the ACL currents are detected by the sensor. In response to the sensor detecting these currents, a processor ascertains that the catheter is passing through the sheath. In the event that a plurality of catheters are used during the procedure, the processor may further identify the catheter from the plurality of catheters, based on the frequencies of the ACL currents. The processor may then show, on the display, the distal portion of the catheter emerging from the sheath, such that it is clear to the viewer that the catheter passes through the sheath.

Apparatus Description

Figure 1:
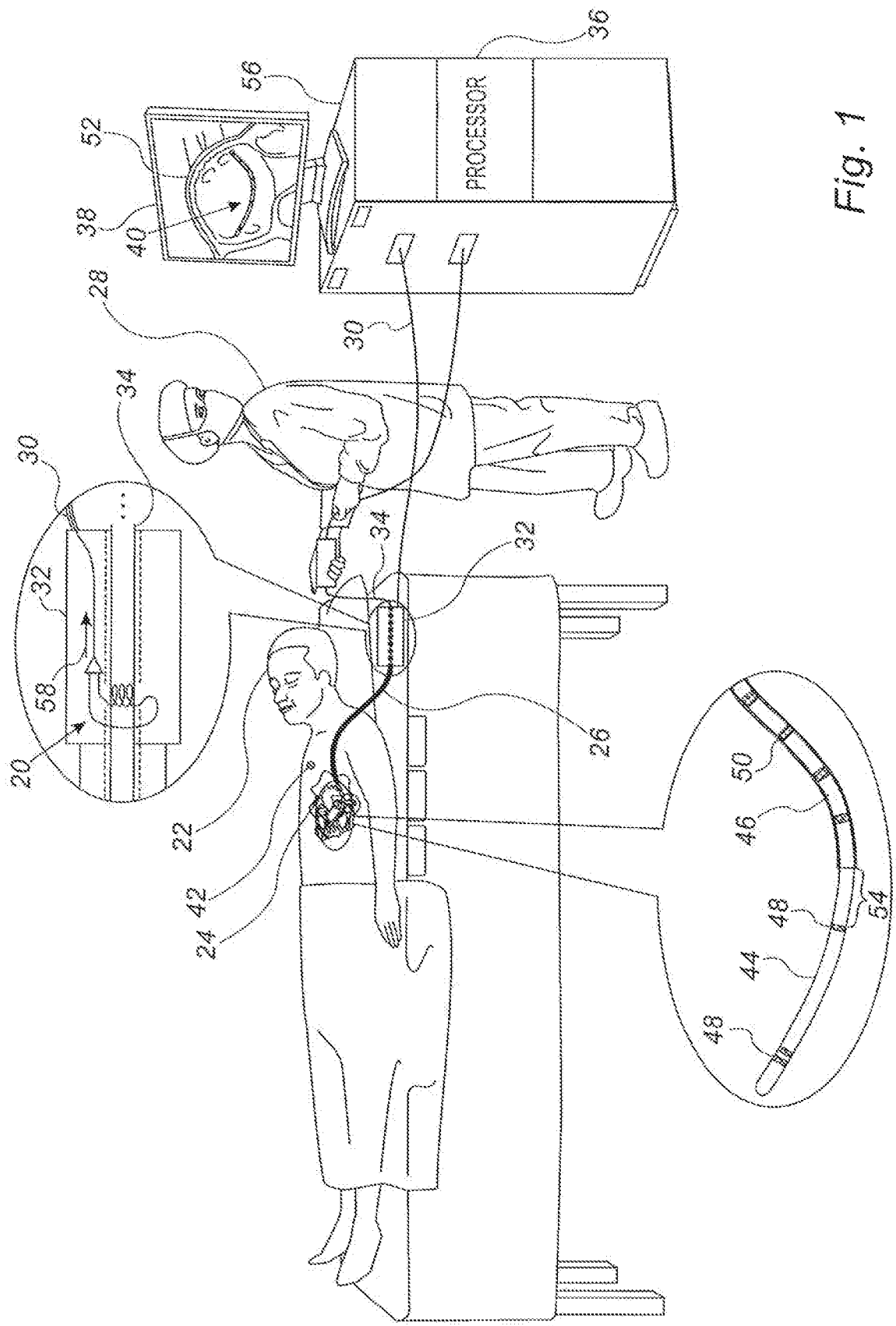
FIG. 1 is a schematic illustration of a sheath comprising a sensor, in accordance with some embodiments of the present invention.

Reference is initially made to FIG. 1, which is a schematic illustration of a sheath 26 comprising a sensor 20, in accordance with some embodiments of the present invention.

By way of example, FIG. 1 depicts a physician 28 performing a procedure on a subject 22. During the procedure, physician 28 inserts sheath 26 into the body of subject 22, and then advances the sheath to the heart 24 of the subject. The physician then inserts a catheter 34, through sheath 26, into the body of the subject. Subsequently, using the sheath, catheter 34 is navigated to heart 24, and the catheter is then used, for example, to map, and/or ablate, the endocardial surface of the heart.

Typically, an ACL tracking system, as described, for example, in U.S. Pat. No. 8,456,182, whose disclosure is incorporated herein by reference, is used to facilitate navigation of the sheath and/or catheter. Such a system includes a set of one or more electrodes 42, which are coupled to the subject's body. For example, in some embodiments, three electrodes 42 are coupled to the subject's chest, and another three electrodes 42 are coupled to the subject's back. The ACL tracking system further includes another set of one or more electrodes 50, which are coupled to the distal portion 46 of the sheath. Typically, to facilitate navigating the sheath, ACL currents are passed from electrodes 50 to electrodes 42, and the resulting current amplitudes are measured at electrodes 42. Based on the ratios between the amplitudes, or between the impedances implied by these amplitudes, and given the known positions of electrodes 42 on the subject's body, a processor 36 ascertains the respective locations of electrodes 50, and hence, the location (relative to the subject's body) and orientation of distal portion 46.

Similarly, one or more electrodes 48 are typically coupled to the distal portion 44 of the catheter. By passing ACL currents between these electrodes and electrodes 42, the location (relative to the subject's body) and orientation of distal portion 44 may be likewise ascertained by processor 36.

Typically, upon ascertaining the respective locations of the distal portions of the catheter and the sheath, processor 36 displays a representation 40 of these portions on a display 38. Typically, the processor displays an image 52 of the interior of the body of the subject, such as an image of a chamber of heart in which the respective distal portions are located, and superimposes representation 40 on a portion of image 52 corresponding to the ascertained locations. Subsequently, physician 28 may refer to image 52, to improve execution of the procedure.

In embodiments of the present invention, a sensor 20 is coupled to the sheath. When catheter 34 passes through the sheath, sensor 20 detects one or more electric currents, such as ACL currents passed from electrodes 48 into the body, passing through the catheter. Responsively to the sensor detecting these currents, processor 36 ascertains that the catheter is passing through the sheath. In response thereto, the processor may, in displaying representation 40, display the distal portion of the catheter emerging from the sheath, such that it is clear to the physician that the catheter is passing through the sheath.

Typically, the proximal portion of sheath 26 is connected, via a cable 30, to a console 56, which typically contains processor 36. Upon sensing a current passing through the catheter (and hence, through the sheath), the sensor outputs a signal 58, which is received by processor 36 via cable 30. Based on output signal 58, the processor ascertains that the sensor detected an electric current passing through the sheath.

It is emphasized that without the detection of the ACL currents by sensor 20, the processor would not necessarily know to show the catheter emerging from the sheath, especially in cases in which all of electrodes 48 are outside of the sheath. In particular, it would be unclear whether a portion 54 of the catheter that is proximal to the proximal most electrode 48 should be shown emerging from the sheath. Hence, the detection of currents by sensor 20 helps the processor generate an accurate display of the catheter.

In some cases, catheter 34 may be one of a plurality of catheters (e.g., of different types) used during the procedure. In such cases, electrodes 48 on catheter 34 typically use different frequencies from those used by the electrodes on the other catheters. Hence, the processor may identify catheter 34 from the plurality of catheters—i.e., the processor may identify that catheter 34, rather than another one of the catheters, is passing through the sheath—responsively to the frequency of the electric current detected by the sensor. (Since the frequency of output signal 58 corresponds to that of the detected electric current, the processor may ascertain the frequency of the electric current from the frequency of output signal 58.)

In some embodiments, the processor increases the level of confidence with which the processor ascertains that a particular catheter is passing through the sheath, in response to the sensor detecting a plurality of electric currents at the different respective frequencies used by electrodes 48.

It is noted that in the context of the present application, including the claims, two items are said to be "coupled to" one another in any case in which the two items belong to a common physical unit. Thus, for example, sensor 20 may be coupled to the sheath by virtue of being coupled externally to the sheath, or alternatively, by virtue of being disposed within the sheath. It is further noted that sensor 20 may be coupled to any suitable portion of the sheath. Typically, however, as assumed for the remainder of the description and in the figures, sensor 20 is disposed within the proximal portion of the sheath, such as within the handle 32 of the sheath.

In general, processor 36 may be embodied as a single processor, or as a cooperatively networked or clustered set of processors. Processor 36 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the processor in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Figure 2B:
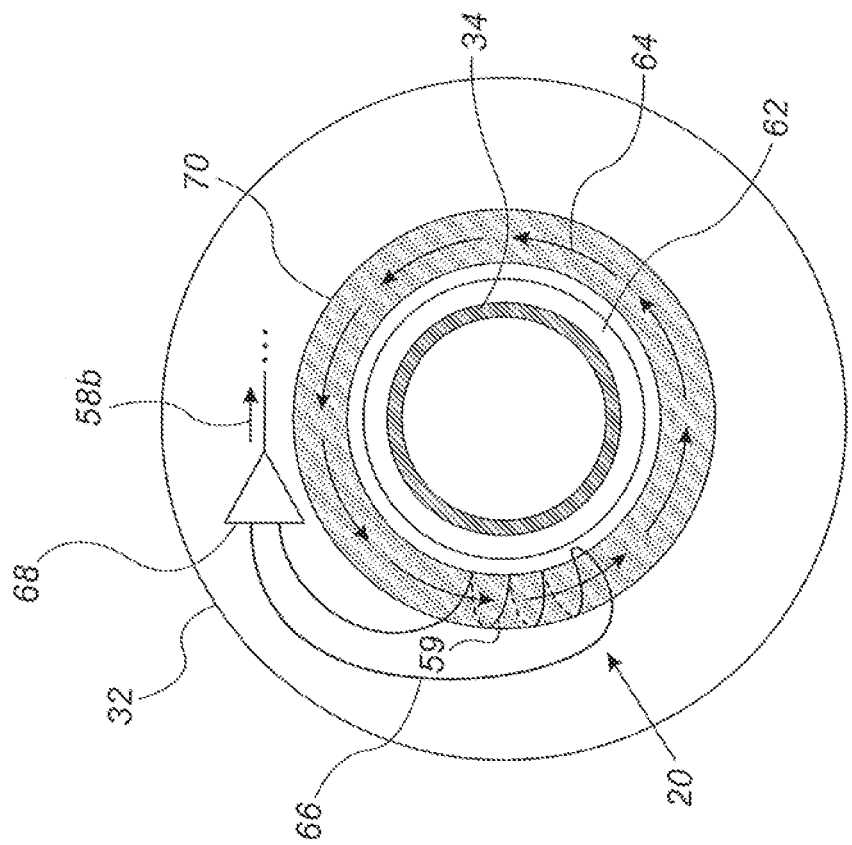
FIGS. 2A-B are schematic illustrations of cross-sections through a handle of a sheath, in accordance with some embodiments of the present invention.
Figure 2A:
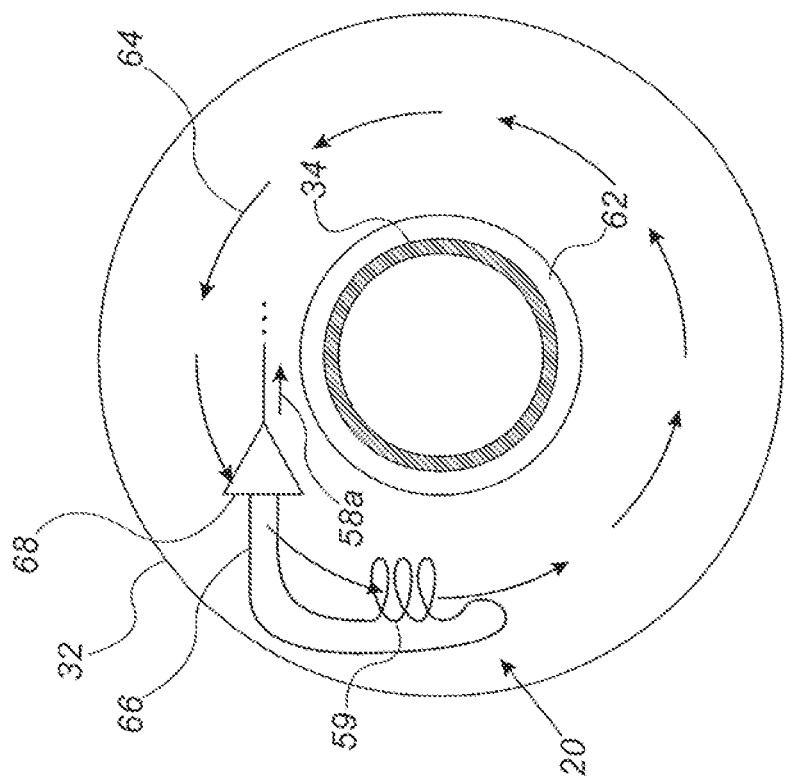

Reference is now made to FIGS. 2A-B, which are schematic illustrations of cross-sections through handle 32 of sheath 26, in accordance with some embodiments of the present invention.

In the embodiment of sensor 20 shown in FIG. 2A, which corresponds to the embodiment shown in FIG. 1, sensor 20 comprises a coil 59, which is disposed within handle 32. As currents pass through catheter 34, which passes through the lumen 62 of the sheath, a magnetic field 64 is generated in the handle. Magnetic field 64 induces a voltage across the two ends of coil 59, and hence, across two leads 66 connected, respectively, to the two ends. An amplifier 68 receives the voltage across leads 66, and generates an output voltage signal 58a responsively thereto. Based on this signal, the processor ascertains that a current is passing through the sheath, the frequency of the current being that of output voltage signal 58a.

In the alternative embodiment of FIG. 2B, sensor 20 additionally comprises a ferrite toroid 70, around which coil 59 is wound. As currents pass through catheter 34, the magnetic field generated in ferrite toroid 70 induces a voltage across leads 66. In this case, leads 66 are typically connected across a resistor inside amplifier 68, and an output current signal 58b is output by the sensor responsively to the current flowing across the resistor. Based on this signal, the processor ascertains that a current is passing through the sheath, the frequency of the current being that of output current signal 58b.

Notwithstanding the particular embodiments shown in FIGS. 2A-B, it is noted that the scope of the present disclosure includes any suitable type of voltage or current sensor.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus for use with a catheter, the apparatus comprising:
   a sheath configured for insertion into a body of a subject, the sheath comprises a proximal portion and a lumen extending through the sheath; and
   a sensor disposed within the proximal portion of the sheath, configured to detect an electric current passing through the catheter, when the catheter passes through the sheath and into the body of the subject, the sensor including ferrite toroid disposed about the lumen of the sheath and a coil wound around the ferrite toroid such that the lumen extends through an opening of the ferrite toroid.

2. The apparatus according to claim 1, wherein the proximal portion of the sheath comprises a handle, and wherein the sensor is disposed within the handle.

3. The apparatus according to claim 1, further comprising a processor, configured to ascertain, responsively to the sensor detecting the electric current, that the catheter passes through the sheath.

4. The apparatus according to claim 3, wherein the processor is further configured to identify the catheter from a plurality of catheters, responsively to a frequency of the electric current detected by the sensor.

5. The apparatus according to claim 3, wherein the processor is further configured to display a representation of a distal portion of the catheter emerging from the sheath, responsively to ascertaining that the catheter passes through the sheath.

6. The apparatus according to claim 5, wherein the sheath comprises a distal portion, and wherein the processor is configured:
   to identify a location, relative to the body of the subject, of the distal portion of the sheath,
   to display an image of an interior of the body of the subject, and
   to display the representation of the distal portion of the catheter emerging from the sheath by superimposing the representation on a portion of the image corresponding to the identified location.

7. The apparatus according to claim 5, wherein the processor is configured:
   to identify a location, relative to the body of the subject, of the distal portion of the catheter,
   to display an image of an interior of the body of the subject, and
   to display the representation of the distal portion of the catheter emerging from the sheath by superimposing the representation on a portion of the image corresponding to the identified location.

8. The apparatus according to claim 7, wherein the processor is configured to identify the location of the distal portion of the catheter responsively to the electric current being passed from an electrode at the distal portion of the catheter.

9. The apparatus according to claim 6, further comprising one or more electrodes coupled to the distal portion of the sheath, wherein the processor is configured to identify the location of the distal portion of the sheath responsively to electric currents passed from the electrodes.

10. A method, comprising:
    using a sensor that is coupled to a sheath, the sheath comprises a proximal portion and a lumen extending through the sheath, the sensor includes ferrite toroid disposed about the lumen of the sheath and a coil wound around the ferrite toroid such that the lumen extends through an opening of the toroid;

detecting an electric current passing through a catheter, when the catheter passes through the sheath and into a body of a subject; and using a processor, ascertaining, responsively to the sensor detecting the electric current, that the catheter passes through the sheath.

11. The method according to claim 10, further comprising, using the processor, identifying the catheter from a plurality of catheters, responsively to a frequency of the electric current detected by the sensor.

12. The method according to claim 10, further comprising, using the processor, displaying a representation of a distal portion of the catheter emerging from the sheath, responsively to ascertaining that the catheter passes through the sheath.

13. The method according to claim 12, further comprising, using the processor:

identifying a location, relative to the body of the subject, of the distal portion of the catheter, and displaying an image of an interior of the body of the subject, wherein displaying the representation of the distal portion of the catheter emerging from the sheath comprises superimposing the representation on a portion of the image corresponding to the identified location.

14. The method according to claim 13, wherein the processor is configured to identify the location of the distal portion of the catheter responsively to the electric current being passed from an electrode at the distal portion of the catheter.

15. The method according to claim 12, further comprising, using the processor:

identifying a location, relative to the body of the subject, of a distal portion of the sheath, and displaying an image of an interior of the body of the subject, wherein displaying the representation of the distal portion of the catheter emerging from the sheath comprises superimposing the representation on a portion of the image corresponding to the identified location.

16. The method according to claim 15, wherein identifying the location of the distal portion of the sheath comprises identifying the location of the distal portion of the sheath responsively to electric currents passed from one or more electrodes coupled to the distal portion of the sheath.

* * * * *